(12) United States Patent
Fischell et al.

(10) Patent No.: US 8,916,741 B2
(45) Date of Patent: Dec. 23, 2014

(54) DEVICE FOR THE RAPID CLOSURE OF WOUNDS AND SURGICAL INCISIONS

(71) Applicants: Robert E. Fischell, Dayton, MD (US); Leigh Vinocur, Owings Mills, MD (US)

(72) Inventors: Robert E. Fischell, Dayton, MD (US); Leigh Vinocur, Owings Mills, MD (US)

(*) Notice: Subject to any disclaimer, the term of this patent is extended or adjusted under 35 U.S.C. 154(b) by 25 days.

(21) Appl. No.: 13/716,390

(22) Filed: Dec. 17, 2012

(65) Prior Publication Data
US 2014/0171849 A1  Jun. 19, 2014

(51) Int. Cl.
*A61F 13/00* (2006.01)
*A61B 17/00* (2006.01)
*A61F 13/02* (2006.01)

(52) U.S. Cl.
CPC ............ *A61F 13/0246* (2013.01); *A61B 17/00* (2013.01)
USPC ................... 602/42; 602/41; 602/43; 602/48; 602/54; 606/213; 606/215; 606/216

(58) Field of Classification Search
CPC A61B 17/00491; A61B 17/085; A61F 13/02; A61F 13/0203; A61L 15/28; A61L 15/58; A61L 15/278

USPC ............ 602/48, 56, 41–43, 53; 606/213–216
See application file for complete search history.

(56) References Cited

U.S. PATENT DOCUMENTS

| | | | | |
|---|---|---|---|---|
| 2,762,371 A | * | 9/1956 | Guio | 606/216 |
| 4,038,989 A | * | 8/1977 | Romero-Sierra et al. | 606/216 |
| 4,141,363 A | * | 2/1979 | James et al. | 606/216 |
| 5,263,970 A | * | 11/1993 | Preller | 606/216 |
| 6,329,564 B1 | * | 12/2001 | Lebner | 602/41 |
| 7,332,641 B2 | * | 2/2008 | Lebner et al. | 602/42 |
| 2007/0038247 A1 | * | 2/2007 | Lebner et al. | 606/215 |

FOREIGN PATENT DOCUMENTS

GB      2223410 A  *  4/1990

* cited by examiner

*Primary Examiner* — Kim M Lewis
(74) *Attorney, Agent, or Firm* — Rosenberg, Klein & Lee

(57) ABSTRACT

A wound closure system having first, second and third adhesive pads with a pair of strap members fixedly secured to the first and third adhesive pads. The pair of strap members are slidably received within the second adhesive pad. When the third adhesive pad is displaced, the first and second adhesive pads are displaced toward each other to close the wound.

19 Claims, 2 Drawing Sheets

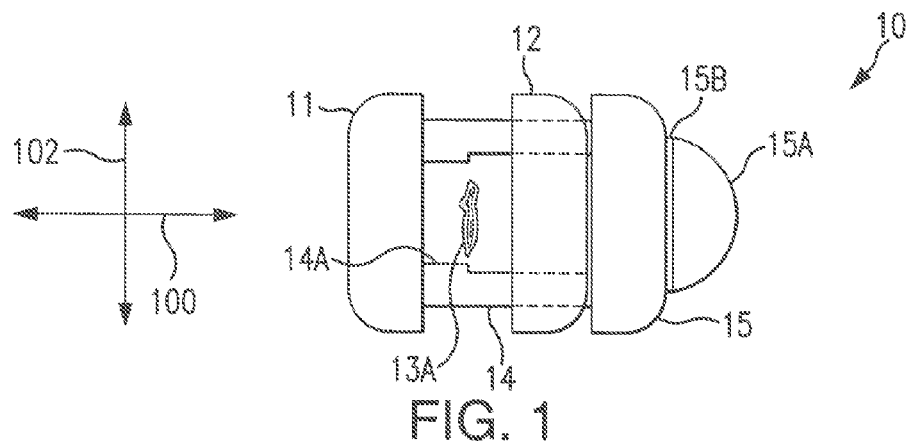
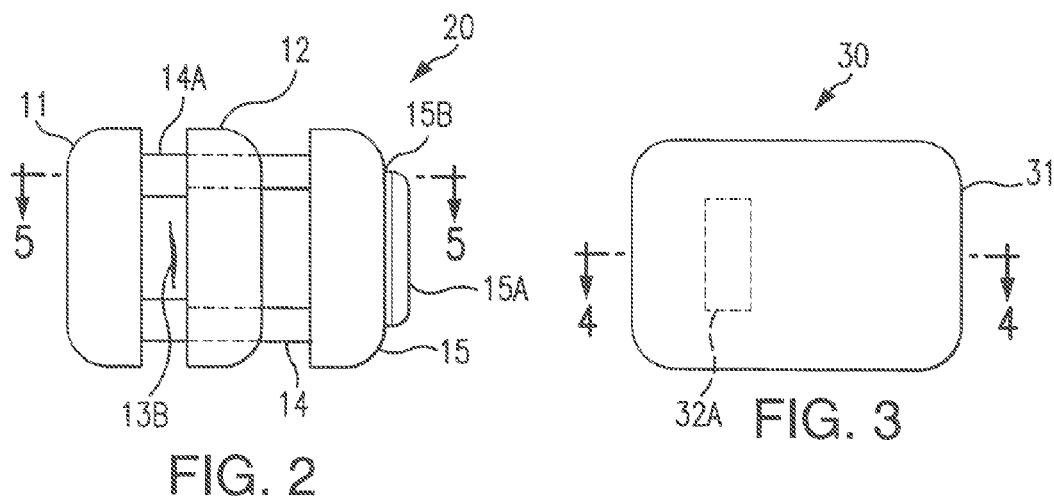
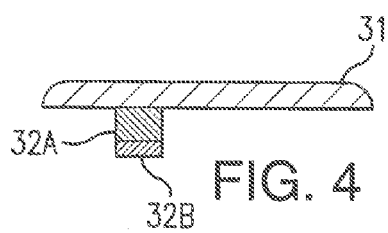
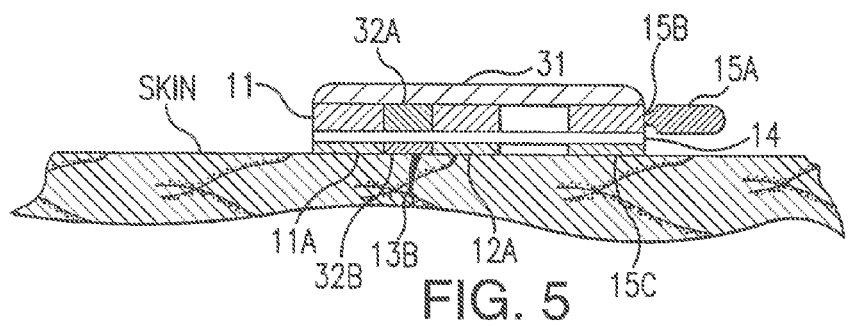

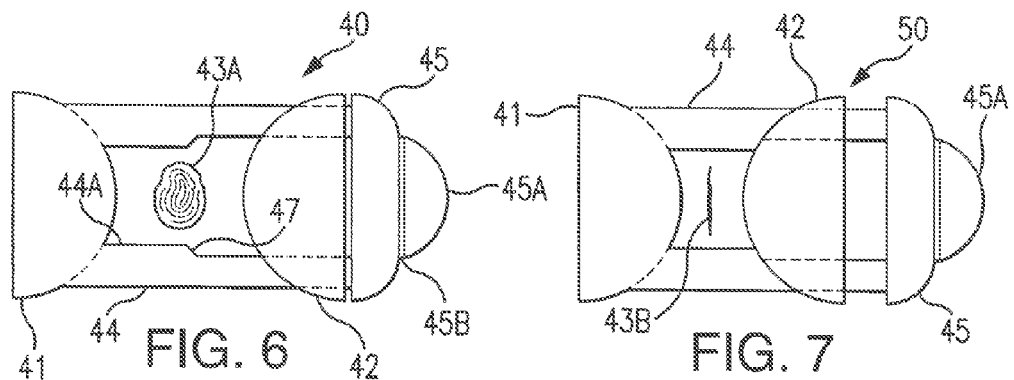
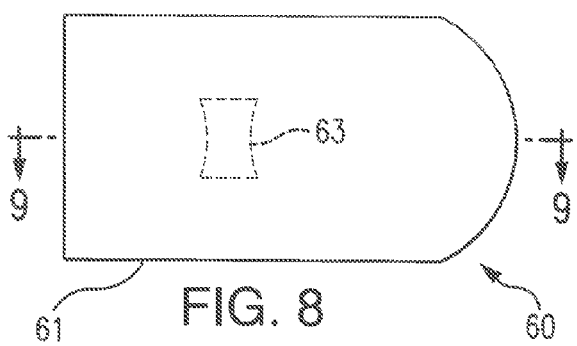
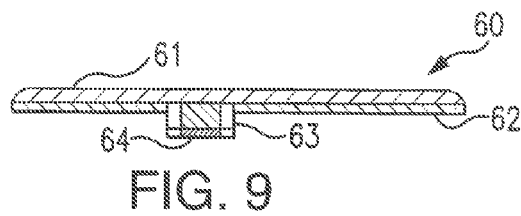
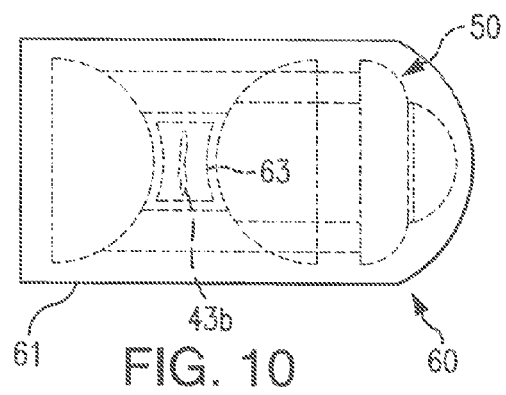

DEVICE FOR THE RAPID CLOSURE OF WOUNDS AND SURGICAL INCISIONS

FIELD OF USE

This invention is in the field of methods and devices for closing a wound in the skin.

BACKGROUND OF THE INVENTION

Present wound closure systems include bandages, stitches, staples, and adhesives. Each of these may be chosen for various types of wounds based on its advantages and disadvantages. However, none of these current solutions provide an elegant closure system for minor to moderate skin wounds without further disturbing the wounded area, increasing scarring, increasing wound care complexity, lengthening healing time, or some combination of the above. Furthermore, in creating a skin incision during the performance of medical procedures such as angiography, stenting, dermatological interventions and minor surgical procedures it is often necessary to uses stitches or other problematic means to close such an incision. The present invention provides a simple, elegant solution to quickly treat minor to moderate skin cuts or wounds without disturbing the cut or wound and minimizing potential scarring. Still further, the wound closure system described herein is particularly suitable for closing incisions in the skin made during either a surgical operation or an interventional procedure.

SUMMARY OF THE INVENTION

The present invention provides a simple and elegant solution to quickly treat minor to moderate skin wounds without disturbing the wound and minimizing potential scarring. Still further, the wound closure system described herein is particularly suitable for closing incisions in the skin made during either a surgical operation or an interventional medical procedure. For much of the description of the present invention, the word "wound" is used to describe a break in the skin caused by an inadvertent break in the skin and it also includes an incision in the skin created for a medical procedure. To the same effect, the word "round" as applied to wounds implies any shape with a substantial but finite amount of skin removed that may be in a circular, ovular, or any other shape that is not essentially a line.

Described herein is an improved wound closure system that uses adhesive pads and two flat straps to close skin wounds. A first adhesive pad is adhesively joined to the skin on one side of, but not in contact with, the wound or incision. A second adhesive pad is adhesively attached to the skin on the opposite side of the skin opening, with flat straps straddling the edges of the two adhesive pads. If the wound is essentially linear, the adhesive pads will be rectangular; if the wound is essentially round or has a generally curved shape, a rounded wound pad would be used in which the first and second adhesive pads are curved. The flat straps are fixedly attached to the first and third adhesive pads and are adapted to slide through the second adhesive pad. The third adhesive pad has an attached pull tab that pulls the flat straps through the second adhesive pad thus forcing the first and second adhesive pads to come together, and thusly closing the skin around the wound. The force exerted by the first two adhesive pads causes the closure of the wound in the skin. The third adhesive pad is then adhesively placed onto the skin outside of the second adhesive pad, bonding the entire wound closure system firmly to the skin.

This closure system would also typically include a cover with a pre-applied antibiotic ointment section mounted onto a pad on the underside of that cover. For the linear wound version, this ointment section is rectangular; for the round wound version of this device, the ointment section is curved in such a way as to fit inside the curved pads when the wound closure device is closed around the wound. Once the wound is closed, the cover is adhesively attached to the three adhesive pads with the ointment section in direct contact with the closed wound. The cover prevents accidental contact with the wound, unintentional removal of the adhesive pads, and protects the wound and wound closure system from invasion of liquids, dirt, debris, and microorganisms that could cause infection or inflammation. The outer edge of the cover may extend only to the boundary of the wound closure device, or it could attach directly to the patient's skin beyond the outer edges of the wound closure device.

The advantages of the present invention are accomplished through a wound closure system that is quick and easy to use. The only part that touches the wound is an antibiotic ointment. Small wounds where bandages are normally applied may bleed through or stick to the bandage, causing pain and increasing healing time. Rather than merely covering the wound, the present invention will close the wound, preventing excessive bleeding that often results from minor abrasions to the head, fingers or other body locations. The wound cover described above will also provide a barrier to debris in the same manner as bandages do, but since it is applied to the entire wound closure device area there will be no direct contact of its adhesive portions with the open wound, thus providing a decreased healing time for the patient.

For larger skin wounds, this device avoids the complications associated with stitches and staples caused by additional skin punctures. The design of the present invention allows a skin wound to be closed to a predetermined extent from which degree of closure the patient will benefit from most, without exacerbating the injury. If a skin wound is severe enough to require a hospital visit, this wound closure device will be more appropriate than current means for administering first-aid care to a patient until a medical practitioner can administer professional medical care. This device will in no way increase the size or severity of a skin wound and is thusly appropriate for providing initial wound closure, even if additional treatment and application of other wound closure techniques is subsequently required.

The present invention will come in a range of sizes so as to be applicable to linear wounds ranging from lengths of one-half inch to four inches, and round wounds with a diameter of up to one inch. Because the adhesive pads and flat straps are both made from a flexible material, the wound closure device will be appropriate for both flat and curved skin surfaces.

Designs that can be used for both linear wounds and round wounds provide more effective patient care. The straight edges of the adhesive pads in the linear wound version of this device provide constant closure force along the length of a linear wound. The edges of the curved adhesive pads in the round wound version of this device will provide increased closure pressure at the center of a round wound, while tapering the force off to each side of the wound. This will ensure that the center of the wound closes adequately without producing excessive and unnecessary force on the edges of the round wound.

An important use for the present invention is for incisions made in the skin for interventional treatments such as the placement of a catheter through the skin at the groin or the wrist. Another use of the wound closure device as described herein would be for incisions made during a surgical procedure such as the removal of a skin cancer or other surgical procedure that require an incision being less than some arbitrary length such as 3 inches or a generally circular excision of skin with a diameter less than one inch.

Thus one object of the present invention is to use an arrangement of adhesive pads and flat straps to quickly and easily close wounds on the skin without irritating the injured area.

Another object of this invention is the ability to close skin wounds of varying lengths, widths, and shapes using a range of sizes of the two versions of the wound closure device, and using adhesive pads that can be brought together to the precise degree as warranted by the nature of the wound.

Still another object of this invention is to provide a separate protective cover for the entire injured site that is included in the package with the adhesive pads, the protective cover having an antibiotic ointment placed on a pad on that cover, the antibiotic ointment being applied to the wound to prevent wound contamination and to promote healing.

Still another object of this invention is to have the wound closure device being designed for specific incisions in the skin that occur during frequently used interventional procedures such as coronary stenting.

Still another object of this invention is to have the wound closure device being designed for specific incisions in the skin that occur during frequently used surgical procedures such as the removal of a skin tumor or any other surgical skin incision that is less than approximately 3 inches long or one inch in diameter.

These and other objects and advantages of this invention will become obvious to a person of ordinary skill in this art upon reading the detailed description of this invention including the associated drawings as presented herein.

BRIEF DESCRIPTION OF THE DRAWINGS

FIG. 1 is a top view of the linear wound closure system where the first and the second adhesive pads have been adhesively attached to the skin.

FIG. 2 is a top view of the linear wound closure system of FIG. 1 with the first two adhesive pads pulled together to close the wound in the skin and the third adhesive pad adhesively attached to the skin and the pull tab being bent perpendicular to the skin.

FIG. 3 is a top view of the protective cover for the wound closure system.

FIG. 4 is a cross section of the protective cover at section 4-4 of FIG. 3.

FIG. 5 is a cross section of the linear wound closure system at section 5-5 of FIG. 2 as it would appear with the protective cover attached and the pull tab being placed parallel to the skin.

FIG. 6 is a top view of the rounded wound closure system where the first and the second adhesive pads have been adhesively attached to the skin.

FIG. 7 is a top view of the round wound closure system with the first two adhesive pads pulled together to close the wound in the skin and the third adhesive pad adhesively attached to the skin and the pull tab placed parallel to the skin.

FIG. 8 is a top view of a large protective cover that is designed to extend past the edges of the wound closure system onto the skin, with the location of the antibiotic pad being on the underside of the cover.

FIG. 9 is a cross section of the protective cover at section 9-9 of FIG. 8.

FIG. 10 is a top view of the large protective cover shown in FIG. 8 with the antibiotic ointment pad placed in contact with the closed round wound and the outer edges of the cover extending beyond the outer edges of the wound closure system.

DETAILED DESCRIPTION OF THE INVENTION

FIGS. 1 and 2 show the linear wound closure system as an arrangement of three adhesive pads 11, 12 and 15, and two straps 14. FIG. 1 shows the open wound closure system 10 prior to deployment and FIG. 2 shows the closed wound closure system subsequent to deployment. Adhesive pads 11 and 12 are first placed firmly on the skin adjacent to, but not touching, the open wound 13A. The design of the present invention provides an exact opening between the edges of the pads 11 and 12 as they are adhesively attached to the skin. Adhesive pad 15 is then pulled to the right using pull tab section 15A in its upward position as shown in FIG. 2. The thin walled, flexible hinge 15B allows the pull tab 15A to be rotated to be essentially perpendicular to the skin to improve the operator's ability to pull on the flat straps 14. By pulling on the tab 15A to the right as shown in FIG. 1, the operator causes the pads 11 and 12 to come together by an exact amount as determined by the positions of the indents or shoulder that mark the extent of the wider portion 14A of the flat straps. Adhesive pad 15 is then adhesively joined to the skin beside adhesive pad 12 so that the wound closure device is now secure. The post-deployment positioning of the adhesive pads 11 and 12 is shown in FIG. 2 showing the closed wound 13B. The correct size of the wound closure system 10 will be chosen by the patient or the operator and will be placed so that straps 14 surround but do not have contact with the wound 13. Thus, the closed wound closure system 20 as shown in FIG. 2 provides quick and easy wound closure without the adhesive pads contacting the injured skin.

First adhesive pad 11 is fixedly secured to third adhesive pad 15 at opposing ends of each strap 14. Second adhesive pad 12 is adapted to be slidably displaceable on each of straps 14 in longitudinal direction 100 which is perpendicular to transverse direction 102. Second adhesive pad 12 includes a pair of through openings having a cross-section sized to accommodate respective straps 14 and this design permits slidable displacement through the adhesive pad 12.

It should also be noted in FIGS. 1 and 2 that each flat strap 14 has a wider section 14A that has a protrusion that provides a precise degree of closure for the wound closure device 10 when the pull tab 15A has been pulled and the adhesive pad 15 has been adhesively attached to the patient's skin. The wider section 14A of the strap 14 when taken with respect to the remaining section of strap 14 creates a shoulder section. The degree of closure could be made to a different extent for different cuts and abrasions of the skin with less of a closing distance between the adhesive pads 11 and 12 when the wound closure device 10 is used for closing a linear skin incision made by a physician during an interventional or a surgical procedure and a greater closure when there is some finite width to the wound 13A.

FIG. 3 is a top view of the protective cover system 30 having a cover 31 onto which an antibiotic pad 32A is attached. An antibiotic coating 32B is placed on the bottom side of the pad 32A. The cover 31 is designed to cover the entire injured area, including adhesive pads 11, 12, and 15, as well as the straps 14 and the entire closed wound 13B as shown in FIG. 5. The cover may or may not extend beyond the perimeter of the wound closure system 20. FIG. 3 shows the location of an antibiotic pad 32A and the ointment 32B both of which are located on the underside of the cover 31. This can be seen clearly in FIG. 4, where the antibiotic ointment 32B will be located on the portion of cover 31 that will be in direct contact with closed wound 13B. There is an adhesive (not shown in FIG. 4) that is on the underside of the cover 31 that attaches the cover 31 to the wound closure system 20. Antibiotic pad 32A will be coated with a thin layer of antibiotic ointment 32B to provide additional wound protection and ease of patient care. A separate ointment application to the wound 13 would then be superfluous. This design for a protective cover system 30 could also go beyond the extent of that shown in FIG. 5 and even go beyond the pull tab 45A, as shown in FIG. 10. This could provide additional protection for the wound or skin incision.

FIG. 5 is the cross section at 5-5 of FIG. 2 showing the cover system 30 adhesively attached to the wound closure system 20 as the cover 31 places the ointment 32B in direct contact with the closed wound 13B. The bottom of adhesive pads 11 12 and 15 will be coated with a thin layer of adhesive 11A, 12A, and 15C respectively to ensure a firm but non-penetrating bond with the skin. The cover 31 protects the entire wound closure device 20 from elements such as moisture or friction that might cause the wound closure system 10 to come off the skin. It should be noted that the cover system 30 can be applied to the linear wound closure device system 20 as shown in FIG. 5, or the round wound closure system 50 as shown in FIG. 10.

FIGS. 6 and 7 depict respectively top views of the open round wound closure system 40 in the pre-deployment setting and round wound closure system 50 in the post-deployment setting. System 40 is used for closing a more open (rounded) wound area depicted by the open wound 43A rather than a more linear wound 13A as shown in FIG. 1. Adhesive pads 41 and 42 are first placed firmly on the skin beside, but not touching, the open wound 43A. Adhesive pad 45 is then pulled to the right using pull tab section 45A. The flexible hinge 45B can be pulled to the right (in FIG. 7) to provide enough tension on the flat straps 44 to close the curved wound 43A to be as shown as the closed wound 43B in FIGS. 7 and 10. FIG. 6 shows the pull tab 45A as it lies parallel to the adhesive pads 41 42 and 45 after those three pads have been adhesively attached to the skin. Depending on the size (and possibly the shape) of the wound, the correct size and curvature of the wound closure system 40 will be chosen. The pads 41 and 42 will be placed so that straps 44 surround but do not have contact with the wound 43. The shoulder 47 limits how much the pads 41 and 42 can be pulled together. This design provides a predetermined compression of the skin by pulling together the pads 41 and 42 for a preset compression of the skin. Thus, the closed wound closure system 50 as shown in FIG. 7 provides quick and easy wound closure without contacting the injured portion of the skin and with a predetermined compression of the skin around the wound.

FIGS. 8, 9 and 10 show the cover system 60 that is designed to cover the wound closure system 50. The cover 61 protects not only the wound closure system 50, but also the skin around the wound closure device to provide maximum protection against elements such as dirt, germs or moisture. The larger wound cover 61 could also be applied to the linear wound closure system 20 of FIG. 2 or the wound closure system 50 shown in FIG. 7. FIGS. 8 and 10 show the outline of the curved antibiotic ointment pad 63 that is located on the cover 61 in such a location as to cause the antibiotic ointment 64 to be placed directly onto the closed wound 43B as seen in FIG. 10. FIG. 9 is a cross sectional view of the cover system 60 as shown at 9-9 in FIG. 8. FIG. 9 shows the antibiotic ointment 64 applied to the curved pad 63 on the lower, adhesive surface 62 side, of the cover 61. FIG. 10 shows the cover system 60 placed over the closed wound closure system 50 with the edges of the cover 61 extending beyond the edges of the closed, wound closure system 50. As with the cover system 30 as shown in FIG. 5, FIG. 10 shows that the cover system 60 applies an antibiotic ointment 64 directly onto the closed wound 43B that protects the wound 43B from infection.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. A wound closure system for closing an open wound on the skin of a patient, the system comprising:
   first, second and third adhesive pads adapted for attachment to the skin of the patient, the first and second pad being initially adhesively attached to the skin on opposite sides of the patient's wound;
   a pair of flat straps fixedly attached to said first and third adhesive pads at opposing sides of said flat straps, said second adhesive pad having a pair of through openings extending throughout an entire longitudinal extension of said second adhesive pad in alignment with said pair of said flat straps whereby the flat straps slide through the second adhesive pad that is positioned between the first and third adhesive pads;
   wherein the wound closure system causes the wound to be closed by using the third adhesive pad to pull on the pair of flat straps to displaced the first and second pads to come towards each other for creating a compression of the skin around the wound, said third adhesive adapted to be subsequently adhered to the patient's skin.

2. The wound closure system of claim 1, where a separate cover system is adhesively attached to the wound closure system after the wound closure system has been used to close the patient's wound and after the first, second and third adhesive pads have been adhesively attached to the patient's skin.

3. The wound closure system of claim 2, where the cover system includes a pad onto which is attached an antibiotic ointment, which antibiotic ointment is placed in contact with the closed wound when the cover system is adhesively attached to the wound closure system.

4. The wound closure system of claim 3, where the cover system is sized to exactly cover the wound closure system.

5. The wound closure system of claim 3 where the cover system is designed to extend beyond the edges of the wound closure system.

6. The wound closure system of claim 1 where the flat straps have indents that provide a preset compression of the skin around the wound when the first and second adhesive pads have been pulled together by appropriate pulling of the flat straps by means of the third adhesive pad.

7. A wound closure system comprising:
   first and second adhesive pads, each of said first and second adhesive pads adapted to be releasably secured to a patient's skin on opposing sides of a wound prior to closure of the wound;
   a third adhesive pad coupled to said first adhesive pad and adapted to be releasably secured to the patient's skin subsequent to closure of the wound; and
   a pair of transversely displaced strap members extending in a longitudinal direction, said first and third adhesive pads being coupled each to the other on opposing longitudinal ends of each of said strap members; said second adhesive pad positioned between said first and third adhesive pads in longitudinal alignment therewith, said pair of strap members being slidably received within said second adhesive pad;

wherein said second adhesive pad has a pair of openings extending throughout an entire longitudinal extension thereof for respective slidable insertion of said strap members therethrough.

8. The wound closure system as recited in claim 7, where said strap member is substantially rectangular in cross-sectional contour.

9. The wound closure system as recited in claim 7, where said first, second and third adhesive pads are substantially rectangular in contour in plan view.

10. The wound closure system as recited in claim 7, where said first and second adhesive pads are arcuately contoured in plan view.

11. The wound closure system as recited in claim 10, where said first and second adhesive pads are formed in a semi-circular contour when taken in plan view.

12. The wound closure system as recited in claim 7, including a cover member for covering an upper surface of said first, second and third adhesive pads.

13. The wound closure system as recited in claim 12, including an antibiotic pad secured to a lower surface of said cover member, said antibiotic pad being adapted for being positioned over and in contact with said wound.

14. The wound closure system as recited in claim 13, including an antibiotic coating secured to a lower surface of said antibiotic pad for direct contact with the wound.

15. The wound closure system as recited in claim 7 including a flexible pull tab secured to an end of said third adhesive pad for displacing said second adhesive pad in said longitudinal direction.

16. The wound closure system as recited in claim 15, where said flexible pull tab includes a flexible hinge joining said pull tab and said third adhesive pad.

17. The wound closure system as recited in claim 7, where each of said strap members includes a shoulder for positioning said second adhesive pad in a predetermined location adjacent said wound.

18. The wound closure system as recited in claim 7, wherein said third adhesive pad is adhered to the skin of said patient subsequent to a displacement of the first and second adhesive pads by a predetermined distance to close said wound.

19. The wound closure system as recited in claim 7, wherein said first and second adhesive pad are releasably secured to said patient's skin opposing sides of said wound.

\* \* \* \* \*